United States Patent [19]

Kamei et al.

[11] Patent Number: 4,596,772
[45] Date of Patent: Jun. 24, 1986

[54] REAGENT FOR ASSAYING CHOLINESTERASE

[75] Inventors: Sachiko Kamei, Tokyo; Kosuke Tomita, Kyoto; Yasunobu Hashimoto, Kyoto; Noriko Inagaki, Kyoto, all of Japan

[73] Assignee: Unitika Ltd., Hyogo, Japan

[21] Appl. No.: 474,940

[22] Filed: Mar. 14, 1983

[30] Foreign Application Priority Data

Mar. 12, 1982 [JP] Japan ................................. 57-39654

[51] Int. Cl.$^4$ .......................... C12Q 1/48; C12Q 1/46
[52] U.S. Cl. ....................................... 435/15; 435/20; 435/832; 435/194
[58] Field of Search ................. 435/15, 20, 21, 194, 435/220, 221, 832

[56] References Cited

U.S. PATENT DOCUMENTS 4,349,631 9/1982 Kagayama ........................... 435/194

FOREIGN PATENT DOCUMENTS 2025088  2/1977  Japan ................................... 435/194
6154992 11/1981  Japan ................................... 435/194

OTHER PUBLICATIONS

Zuber, H. (1978), Comparative Studies of Thermophilic and Mesophilic Enzymes, In: *Biochemistry of Thermophily*, Friedman (ed.) Acad. Press.
Takatori, T. (1975), A Colorimetric Micromethod for the Determination of Serum Cholinesterase Activity, Jap. J. Clin. Chem 4(2): 186–189.

*Primary Examiner*—Sam Rosen
*Assistant Examiner*—Cynthia Lee Foulke
*Attorney, Agent, or Firm*—Sughrue, Mion, Zinn Macpeak & Seas

[57] ABSTRACT

A cholinesterase-assaying reagent containing acetylcholine, a thermostable acetate kinase, and adenosine triphosphate is disclosed. This reagent makes it possible to assay cholinesterase, whose activity is clinically important, with good reproducibility and high accuracy.

22 Claims, 1 Drawing Figure

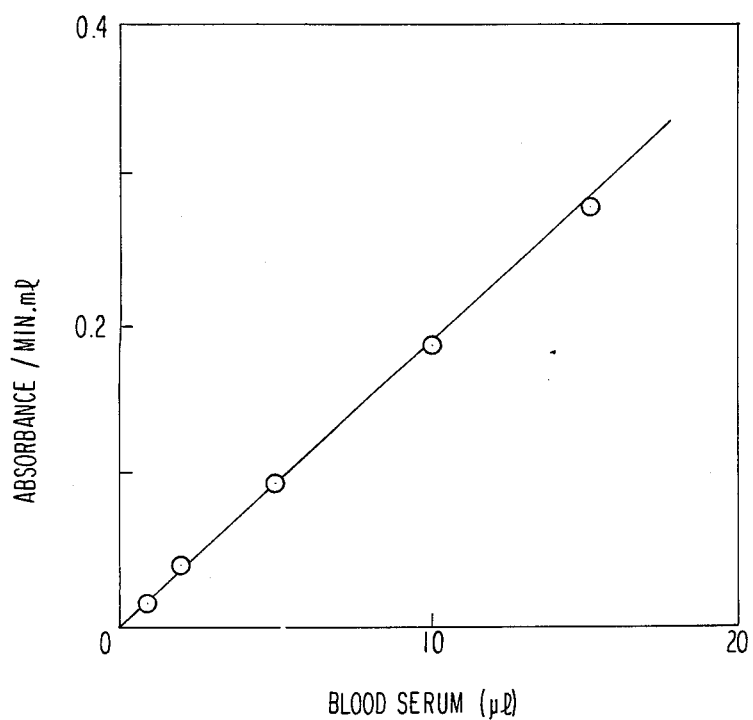

REAGENT FOR ASSAYING CHOLINESTERASE

FIELD OF THE INVENTION

The present invention relates to a reagent for assaying cholinesterase (hereinafter abbreviated as ChE).

BACKGROUND OF THE INVENTION

Recently there has been progress with respect to obtaining information on the relation between enzymes and diseases. Accordingly, there is a general need to assay the activity of enzymes in vitro in order to diagnose diseases. ChE is one enzyme typically assayed in vitro. Its activity is closely related to liver function. An assay of its activity is generally carried out to diagnose liver disease.

In clinical laboratories or the like, ChE is at present assayed by, for example, the following processes:

(1) a process of using acetylcholine as a substrate and measuring the change in pH;

(2) a process of using thiocholine ester as a substrate and measuring the amount of released SH group; and (3) a process of using benzoylcholine or the like as a substrate and measuring the amount of released choline as $H_2O_2$ using a choline oxidase.

Process (1) is a standard process which has been employed in laboratories for a long time. However, its accuracy is poor because it is difficult to maintain the optimum pH and any pH-change does not necessarily correspond to the degree of change in color of an indicator. Accordingly, processes (2) and (3) are taking the place of process (1). However, process (2) still has a problem of error due to the coexistent SH compound, and process (3) has problems in connection with determination of $H_2O_2$ and a problem because phenol in color formation causes interference with the assay system. Thus, no satisfactory processes have been developed. These processes are also inconvenient because even though activities assayed by these processes are presented in terms of "international units", the normal level range of ChE varies greatly depending upon the process employed, resulting in confusion in laboratories. Accordingly, there has been a need for the standardization of the assay of ChE and there has been a tendency to examine process (1). Under the abovedescribed situation, a more accurate process based on process (1) could be the most satisfactory process. However, no such processes are presently known.

One known process involves using acetylcholine as a substrate. Two enzymes of an acetate kinase and a pyruvate kinase act on acetate released from the substrate by the action of ChE to thereby produce pyruvate. The pyruvate is then reacted with a chromogen to produce a dye which is measured by colorimetry (T. Takatori, *Japan. J. Clin. Chem.*, Vol. 4, No. 2, 1975, pp. 186–189). However, this process is not desirable because non-thermostable acetate kinase yielded by bacteria growing at ordinary temperature (*Escherichia coli*) are used. Accordingly, the usable concentration range of the acetate kinase is extremely narrow. Therefore, the values obtained fluctuate, greatly making reproducibility poor. The accuracy of the process is not good, making the process impractical.

SUMMARY OF THE INVENTION

An object of the present invention is to provide a reagent for assaying ChE, which allows an acetate kinase to be used in an extremely wide concentration range, making the reagent very practical.

Another object of the present invention is to provide a reagent for assaying ChE with good reproducibility and accuracy.

As a result of intensive investigations to attain the above-described objects, the inventors have found that the use of a thermostable acetate kinase eliminates the defects with the aforesaid composition reported by T. Takatori and provides a reagent which can be used without difficulty at about room temperature usually employed in clinical laboratories.

The present invention provides a ChE-assaying reagent containing acetylcholine, an acetate kinase, and adenosine triphosphate, said acetate kinase being a thermostable acetate kinase.

The assaying reagent of the present invention can contain an acetate kinase in a concentration of an extremely wide range, making the reagent very practical. In addition, it makes it possible to conduct an assay with good reproducibility and high accuracy, giving a definite value.

BRIEF DESCRIPTION OF THE DRAWINGS

The FIGURE is a graph showing the relationship between the amount of control serum in 0.5 ml of a reaction solution and the change in absorbance at 340 nm, with the amount of control serum as the abscissa and absorbance as the ordinate.

DETAILED DESCRIPTION OF PREFERRED EMBODIMENT

The reagent of the present invention is described in detail below. Acetylcholine is used as a substrate. When ChE in a vital sample acts thereon, the substrate is hydrolyzed into acetate and choline. In process (1) described hereinbefore, the pH-change due to the hydrolysis is measured in this stage. If an acetate kinase is allowed to exist in the system, acetate is in turn converted to acetylphosphate in the presence of a cosubstrate of adenosine triphosphate (hereinafter abbreviated as ATP).

These reactions are shown below.

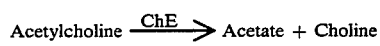

Acetylphosphate + Adenosine diphosphate

An acetate kinase specifically acts on acetate, and does not act on other organic inorganic acids even when they coexist in the system. The amount of acetylphosphate or adenosine diphosphate (hereinafter abbreviated as ADP) produced is then determined in order to complete the assay of ChE, particularly, the latter is preferable.

The amount of the ADP can be determined by reacting it with phosphoenolpyruvate in the presence of a pyruvate kinase and determining the amount of ADP based on the amount of pyruvate. The amount of pyruvate can be determined by a reaction with a proper chromogen as a hydrazine compound or NADH (see the note below) in the presence of a lactate dehydrogenase. The latter process is an extremely advantageous process because the entire reactions are carried out enzymatically. Accordingly, the process is not likely to be influenced by the presence of other materials. The reactions are shown below.

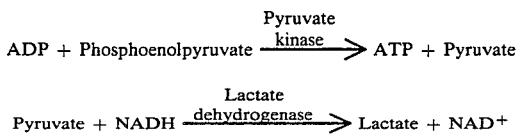

(In the above formula, NADH represents a reduced form β-nicotinamide adenine dinucleotide, and NAD+ represents an oxidized form β-nicotinamide adenine dinucleotide.)

Highly accurate determination of ADP can be conducted with ease by measuring the change in absorbance of NADH in UV region (340 nm). In addition, since the produced ADP can be again converted to ATP by the action of phosphoenolpyruvate in the presence of the pyruvate kinase, the action of acetate kinase on acetate is enhanced making it possible to obtain an extremely sensitive measurement.

The acetate kinase to be used in the present invention must be a thermostable acetate kinase. The thermostable acetate kinase, for example, is yielded by microorganisms whose optimum growth temperature is 50° C. to 85° C., preferably 60° C. to 85° C. The phrase "thermostable acetate kinase" as used herein in the present invention means an acetate kinase which shows a maximum residual activity of 80% or more, preferably 90% or more, optimally about 100%, of the original activity in the heat-resisting test to be described hereinafter. The test on heat resistance is conducted by treating an acetate kinase in a 50° C. buffer solution for 15 minutes. Concentration and pH of the buffer solution are properly adjusted depending upon the kind of acetate kinase to be tested. In general, the concentration is 5 mM to 500 mM, preferably 10 mM to 100 mM, and pH ranges from 2 to 11, preferably 5 to 9. With acetate kinase illustrated in the present invention, a concentration of about 50 mM and a pH of 6.5 to 8.0 are suitable. Activity is assayed by the method described in *Methods in Enzymology*, Vol. 44, p 335 (1976) according to the reverse reaction system described in *J. Biol. Chem.*, Vol. 249, p. 2567 (1974).

In the present invention, any acetate kinase can be used that satisfies the above-described condition. As such acetate kinase, there are illustrated those yielded by *Bacillus stearothermophilus*, *Clostridium thermoaceticum*, *Pseudomonas thermoaminolyticus* V-2 (FERM P-2917), etc. In view of easy purification and high specific activity, acetate kinase yielded by *Bacillus stearothermophilus* is particularly preferable. Such acetate kinase can be obtained, as is described in, for example, *J. Biochem.*, 84, 193 (1978), by culturing the microorganisms in a medium for culturing ordinary microorganisms containing a carbon source such as glucose, saccharose, molasses or malic acid and a nitrogen source such as ammonium sulfate, urea, peptone, meat extract or amino acids and, if necessary, inorganic salts and/or vitamins, and, if necessary, purified in a manner usually employed in purifying enzymes.

When the reaction systems are conducted enzymatically, a pyruvate kinase and a lactate dehydrogenase are used as described above. These enzymes are not necessarily thermostable. It is possible to use various ordinary enzymes of microorganism origin or animal tissue origin. With the pyruvate kinase, the use of thermostable enzymes yielded by thermophilic bacteria such as *Bacillus stearothermophilus* or by microorganisms of the genus Thermus are advantageous with respect to their stability.

The reagent of the present invention is prepared by, for example, incorporating a thermostable acetate kinase and ATP in a conventional reagent. The amounts to be incorporated are as follows. When conducting the whole reaction systems enzymatically, 1 to 300 mM, desirably 20 to 200 mM, more desirably 30 to 150 mM, of acetylcholine, 1 to 70 U/ml, desirably 5 to 50 U/ml, more desirably 7 to 30 U/ml, of a thermostable acetate kinase, 1 to 30 mM, desirably 1.5 to 15 mM, more desirably 2 to 13 mM, of ATP, 1 to 40 U/ml, desirably 3 to 30 U/ml, more desirably 5 to 20 U/ml, of pyruvate kinase, 0.07 to 30 U/ml, desirably 1 to 20 U/ml, more desirably 2 to 15 U/ml, of a lactate dehydrogenase, 0.07 to 3.0 mM, desirably 0.1 to 2.0 mM, more desirably 0.2 to 1.7 mM, of phosphoenolpyruvate, and 0.07 to 1.5 mM, desirably 0.1 to 1.0 mM, more desirably 0.15 to 0.5 mM, of NADH are used. The above-described ranges also apply when carrying out the reaction with a chromogen, with the lower limit of the desirable amount of thermostable acetate kinase being reducable to 3 U/ml.

When using the reagent of the present invention, the reaction temperature is suitably a temperature which is employed in an ordinary clinical examination, for example, 25° C., 30° C. or 37° C., and the pH is, for example, 6.5 to 8.5, with 7.0 to 8.0 being particularly preferable. A reaction time of several minutes, preferably 1 min to 5 min, suffices when all reactions are conducted enzymatically.

The assaying reagent of the present invention makes it possible to use an acetate kinase in an extremely wide concentration range. Thus, use of the reagent is very practical making it possible to assay ChE with good reproducibility and accuracy, giving a definite value.

The present invention will now ben described in more detail by the following non-limiting examples.

EXAMPLE 1

20 U/ml of an acetate kinase yielded by *Bacillus stearothermophilus* was added to a potassium phosphate buffer solution (50 mM; pH 7.2) containing 5 mM of ATP, 1 mM of phosphoenolpyruvate, 0.3 mM of NADH, 20 mM of magnesium chloride, 10 U/ml of pyruvate kinase, 10 U/ml of lactate dehydrogenase, and 50 mM of acetylcholine chloride to prepare a reagent solution.

Then, control serum was added to the reagent solution in varying volumes, followed by making the total amount 0.5 ml. Enzymatic reaction was conducted at 37° C. for 3 minutes, followed by measuring the change in absorbance of NADH at 340 nm. The results of the measurements were plotted to obtain a standard curve having a good linear relationship as shown in the FIGURE.

EXAMPLE 2

The same procedures as described in Example 1 were repeated except for using an acetate kinase yielded by *Clostridium thermoaceticum*. As a result, a good linear relationship was obtained similar to that shown in the FIGURE.

EXAMPLE 3 AND COMPARATIVE EXAMPLE 1

10 μl of control serum was added to a potassium phosphate buffer solution (50 mM, pH 7.2) containing 5 mM of ATP, 1 mM of phosphoenolpyruvate, 10 mM of magnesium chloride, 5 U/ml of a pyruvate kinase, and 50 mM of acetylcholine chloride to prepare a reagent solution (total amount: 0.5 ml). Then, 1 to 10 U/ml of an acetate kinase yielded by *Bacillus stearothermophilus* was added to this reagent solution, followed by conducting the reaction at 37° C. for 5 minutes. Subsequently, 1.5 mM of 2,4-dinitrophenylhydrazine was added thereto as a chromogen, and the resulting mixture was left at room temperature for 15 minutes. This reaction was discontinued by adding thereto 2 ml of 0.5 N NaOH. When the activity of the ChE was assayed based on the absorbance at 440 nm, the acetate kinase provided a definite value in a wide concentration range of 3 to 10 U/ml. That is, usable concentration range of the acetate kinase is so wide that the enzyme is found to be quite practical.

On the other hand, the usable concentration range was similarly examined by using 1 to 10 U/ml of non-thermostable acetate kinase yielded by *Escherichia coli* for comparison. In this case, it was found that the ChE activity showed a peak when 5 U/ml of the enzyme was used, and sharply decreased before and after the peak, thus a definite value was not obtained.

That is, the acetate kinase in accordance with the present invention shows such a wide usable concentration range that it has great practical usefulneess. In comparison, when conducting an assay using the comparative non-thermostable acetate kinase it is difficult to determine its concentration. And, therefore, it does not have much practical usefulness.

EXAMPLE 4 AND COMPARATIVE EXAMPLE 2

The reaction solution described in Example 1 (containing enzymes and not containing acetylcholine chloride) was stored at 4° C. for 6 days, and 50 mM of acetylcholine chloride was added just before assay. The resulting reagent was used in the same manner as in Example 1 to assay ChE activity. Thus, 91% activity was obtained based on the activity assayed before 6 days.

On the other hand, ChE activity was assayed in the same manner as described above except for using a non-thermostable acetate kinase yielded by *Escherichia coli* for comparison. The activity thus obtained was only 22% based on the activity assayed before 6 days.

That is, the reagent of the present invention can be used to provide much more stable and accurate assaying than the comparative reagent.

While the invention has been described in detail and with reference to specific embodiments thereof, it will be apparent to one skilled in the art that various changes and modifications can be made therein without departing from the spirit and scope thereof.

What is claimed is:

1. A cholinesterase-assaying reagent, comprising: acetylcholine; a thermostable acetate kinase; and adenosine triphosphate.

2. A reagent as claimed in claim 1, further comprising: phosphoenolpyruvate; a pyruvate kinase; and a hydrazine compound.

3. A reagent as claimed in claim 2, wherein said thermostable acetate kinase is contained in an amount of 1 to 70 U/ml.

4. A reagent as claimed in claim 2, wherein said pyruvate kinase is contained in an amount of 1 to 40 U/ml and said phosphoenolpyruvate is contained in an amount of 0.07 to 3.0 mM.

5. A reagent as claimed in claim 2, wherein said pyruvate kinase is contained in an amount of 3 to 30 U/ml and said phosphoenolpyruvate is contained in an amount of 0.1 to 2.0 mM.

6. A reagent as claimed in claim 2, wherein said pyruvate kinase is contained in an amount of 5 to 20 U/ml and said phosphoenolpyruvate is contained in an amount of 0.2 to 1.7 mM.

7. A reagent as claimed in claim 1, further comprising: phosphoenolpyruvate; a pyruvate kinase; and a lactate dehydrogenase.

8. A reagent as claimed in claim 7, wherein said pyruvate kinase is contained in an amount of 1 to 40 U/ml, said lactate dehydrogenase is contained in an amount of 0.07 to 30 U/ml and said phosphoenolpyruvate is contained in an amount of 0.07 to 3.0 mM.

9. A reagent as claimed in claim 7, wherein said pyruvate kinase is contained in an amount of 3 to 30 U/ml, said lactate dehydrogenase is contained in an amount of 1 to 20 U/ml and said phosphoenolpyruvate is contained in an amount of 0.1 to 2.0 mM.

10. A reagent as claimed in claim 7, wherein the pyruvate kinase is contained in an amount of 5 to 20 U/ml, the lactate dehydrogenase is contained in an amount of 2 to 15 U/ml and the phosphoenolpyruvate is contained in an amount of 0.2 to 1.7 mM.

11. A reagent as claimed in claim 1, wherein said thermostable acetate kinase is an acetate kinase yielded by microorganisms having an optimum growth temperature of 60° C. to 85° C.

12. A reagent as claimed in claim 11, wherein the microorganism is *Bacillus stearothermophilus*.

13. A reagent as claimed in claim 1, wherein the acetate kinase has a maximum residual activity of 80% or more.

14. A reagent as claimed in claim 3, wherein the acetate kinase has a maximum residual activity of 90% or more 15. A reagent as claimed in claim 14, wherein the acetate kinase has a maximum residual activity of about 100%.

16. A reagent as claimed in claim 1, wherein the adenosine triphosphate is present in an amount of 1 to 30 mM.

17. A reagent as claimed in claim 1, wherein the thermostable acetate kinase is contained in an amount of one to 70 U/ml, the adenosine triphosphate is present in an amount of 1 to 30 mM and the acetylcholine is present in an amount of 1 to 300 mM.

18. A reagent as claimed in claim 1, wherein the acetate kinase is contained in an amount of 5 to 50 U/ml, the acetylcholine is contained in an amount of 20 to 200 mM and the adenosine triphosphate is present in an amount of 1.5 to 15 mM.

19. A reagent as claimed in claim 1, wherein the acetate kinase is contained in an amount of 7 to 30 U/ml, the acetylcholine is contained in a range of 30 to 150 mM and the adenosine triphosphate is present in an amount of 2 to 13 mM.

20. A method for assaying cholinesterase using the cholinesterase assaying reagent of claim 1.

21. A method as claimed in claim 20, wherein assaying of cholinesterase is carried out at room temperature.

22. A method as claimed in claim 20, wherein assaying of cholinesterase is carried out at about room temperature.

* * * * *